United States Patent [19]

Gubisch et al.

[11] Patent Number: 6,015,928
[45] Date of Patent: Jan. 18, 2000

[54] PROCESS FOR THE PRODUCTION OF HIGHER OXO ALCOHOLS

[75] Inventors: Dietmar Gubisch, Marl; Klaus Armbrust, Duelman; Alfred Kaizik, Marl; Bernhard Scholz, Marl; Rudolf Nehring, Marl, all of Germany

[73] Assignee: Huels Aktiengesellschaft, Marl, Germany

[21] Appl. No.: 08/991,005

[22] Filed: Dec. 15, 1997

[30] Foreign Application Priority Data

Dec. 24, 1996 [DE] Germany .................. 196 54 340

[51] Int. Cl.$^7$ .................. C07C 27/22; C07C 31/125
[52] U.S. Cl. .................. 568/882; 568/451; 568/454; 568/887; 502/28
[58] Field of Search .................. 568/449, 450, 568/451, 454, 904, 909, 882, 883; 502/28

[56] References Cited

U.S. PATENT DOCUMENTS

| | | | |
|---|---|---|---|
| 3,929,898 | 12/1975 | Nienburg et al. | 260/604 HF |
| 4,153,795 | 5/1979 | Matsuda | 546/2 |
| 4,329,521 | 5/1982 | Homeier et al. | 568/909 |
| 5,406,006 | 4/1995 | Hill et al. | 568/882 |
| 5,463,147 | 10/1995 | Bahrmann et al. | 568/882 |
| 5,600,031 | 2/1997 | Roussel | 568/882 |

FOREIGN PATENT DOCUMENTS

| | | |
|---|---|---|
| 0 424 767 A2 | 5/1991 | European Pat. Off. . |
| 21 39 630 | 2/1973 | Germany . |
| 22 06 252 | 8/1973 | Germany . |
| 22 44 373 | 4/1974 | Germany . |
| WO 93/24438 | 12/1993 | WIPO . |

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A single-stage process is described that includes simultaneously, in a mixture containing an olefin; synthesis gas; a cobalt catalyst in an organic phase; and an aqueous cobalt salt solution; hydroformylating the olefin, and forming and extracting into the organic phase the cobalt catalyst from the aqueous cobalt salt solution. An apparatus is also described that includes a means for carrying out the process. The process is particularly suitable for preparing aldehydes and alcohols.

18 Claims, No Drawings

PROCESS FOR THE PRODUCTION OF HIGHER OXO ALCOHOLS

BACKGROUND OF THE INVENTION

1. Field of the Invention

The present invention relates to a process for the production of alcohols by hydroformylating olefins with synthesis gas in the presence of an organic phase containing a cobalt catalyst and subsequent hydrogenation of the aldehydes thus obtained. The cobalt catalyst is formed by reacting an aqueous cobalt salt solution in the presence of an organic solvent, which is only slightly miscible with water or not at all, with synthesis gas. The organic phase containing the cobalt catalyst is obtained by extraction of the cobalt catalyst formed from the aqueous phase by means of an organic extractant which is only slightly miscible with water or not at all.

In addition, the invention relates to the use of the alcohols produced for the production of carboxylic acid esters as plasticizers for plastics.

2. Discussion of the Background

The hydroformylation of olefins with carbon monoxide and hydrogen to give aldehydes having one more carbon atom than the olefin in the presence of transition metal catalysts such as, for example, cobalt and rhodium compounds, is known as the oxo synthesis. In general, a high proportion of straight-chain aldehydes, which are the intermediates in the production of the economically important plasticizer alcohols for plastics and detergent alcohols, is desired in the hydroformylation of olefins to give aldehydes.

While linear and terminal olefins (so-called α-olefins) can very readily be hydroformylated with phosphine-modified rhodium or cobalt catalysts (J. Falbe, Editor, "New Synthesis with Carbon Monoxide", Springer-Verlag, Berlin 1980, pages 55 et seq.,) unmodified cobalt and rhodium catalysts are preferentially employed for low-reactivity olefins, internal olefins, and internal and branched olefins.

In the presence of modified catalysts, internal and branched olefins are hydroformylated very slowly or only partially. This precludes the potential use of modified catalysts for the economical hydroformylation of internal and branched olefins.

The hydroformylation of polymeric and isomeric olefin mixtures containing terminal and internal as well as internal and branched olefins is advantageously carried out with unmodified cobalt catalysts. As compared with rhodium catalysts, higher yields of the valuable straight chain aldehydes are obtained with cobalt catalysts, starting from the same initial olefin.

Examples of typical polymeric and isomeric olefin mixtures, which are preferably converted by cobalt-catalyzed hydroformylation to give the corresponding oxo aldehydes, are the dimers, trimers and tetramers of propene, n-butenes (1- and 2-butene), and isobutene.

According to the known processes, cobalt-catalyzed hydroformylation is carried out as a multi-stage process that includes four process stages: (1) the preparation of the catalyst (precarbonylation), (2) the catalyst extraction, (3) the olefin hydroformylation, and (4) the removal of the catalyst from the reaction product (decobalting). Since the development of the oxo synthesis, the individual process stages of the cobalt-catalyzed hydroformylation are continually being improved and modified.

In the first process stage, the precarbonylation, the catalyst complex ($HCo(CO)_4$) required for the hydroformylation is prepared starting from an aqueous cobalt salt solution by reaction with carbon monoxide and hydrogen. According to DE-OS 2,139,630, the precarbonylation is preferably carried out at temperatures from 100 to 160° C. and under synthesis gas pressures from 200 to 300 bar in the presence of activated carbon, zeolites or basic ion exchangers loaded with cobalt carbonyls.

DE-OS 2,244,373 describes an improved continuous carbonylation process, in which marked shortening of the reaction time is achieved by concurrently passing the starting materials, synthesis gas and aqueous cobalt salt solution, in the presence of oxygen-containing organic solvents, which are poorly miscible with water or not at all, through a zone in which a turbulent flow is maintained. As an advantageous embodiment, the use of a pressurized turbulence pipe for maintaining the turbulent flow and the addition of alcohols or aldehydes having 4 to 10 carbon atoms as the organic solvent are mentioned.

In the second process stage, the catalyst extraction, the cobalt catalyst prepared in the first process stage is extracted from the aqueous phase with an organic phase, preferably the olefin which is to be hydroformylated. According to DE-OS 2,106,252, it is expedient to employ for the catalyst extraction, in addition to the olefin, the reaction products and by products of the hydroformylation, provided they are water-insoluble and liquid under the selected reaction conditions. The catalyst extraction is preferably carried out in a countercurrent at temperatures from 20 to 100° C. and under synthesis gas pressures from 100 to 400 bar. After the phase separation, the organic phase loaded with the cobalt catalyst is fed to the third process stage, the hydroformylation.

From DE-OS 2,139,630, it is known that, in the third process stage, the hydroformylation, olefins loaded with the cobalt catalyst can be hydroformylated in a high-pressure reactor with synthesis gas at temperatures between 70 and 170° C. and at pressures from 100 to 400 bar to give the corresponding aldehydes. Some of the aldehydes formed can be hydrogenated to the alcohol under the hydroformylation conditions, particularly at high temperatures.

The reaction product that, in addition to the valuable aldehyde and alcohol, contains by-products, residual olefin which is not hydroformylated and the cobalt catalyst, is let down to 1 to 15 bar and then fed to the catalyst reprocessing stage.

In the fourth process stage, the decobalting, the organic phase of the reaction product is freed of the cobalt carbonyl complexes in the presence of complex-free process water by treatment with oxygen or air. According to WO 93/24438, the decobalting is carried out at temperatures from 60 to 100° C. and pressures from 1 to 20 bar. In this way, the cobalt catalyst is oxidatively destroyed and the resulting cobalt salts are back-extracted into the aqueous phase. The resulting aqueous cobalt salt solution from the decobalting is recycled into the first process stage, the precarbonylation.

A further embodiment is described in WO 93/24437 and EP-OS 0,183,546. In this case, gas scrubbing with synthesis gas or nitrogen is performed before the oxidative destruction of the cobalt catalyst.

After the gas phase has been separated off, the reaction products in the remaining organic phase are converted to the corresponding alcohols in further processing stages, such as hydrogenation and distillation.

The known multi-stage production processes for oxo aldehydes in the presence of cobalt catalysts have a number of industrial disadvantages. Two expensive process stages, precarbonylation and catalyst extraction, are required for preparing the cobalt catalyst needed for hydroformylation. Due to the mass transfer processes occurring in the two process stages, namely gas/liquid mass transfer in the precarbonylation and liquid/liquid mass transfer in the catalyst extraction, two separate pressure-resistant modules, for example, stirred vessels or packed columns, are necessary. The actual hydroformylation subsequently takes place in a separate pressure reactor. The removal of the cobalt catalyst is tied to a further plant section.

Therefore, the known multi-stage hydroformylation processes necessarily require a very high investment, in addition to a large process engineering effort.

The present invention is therefore based on the object of developing a novel hydroformylation process for olefins and subsequent hydrogenation of the resulting aldehydes that is more economical and easier to carry out in process engineering terms.

It has now been found, surprisingly, that the formation of the cobalt catalyst, the extraction of the cobalt catalyst formed into the organic phase and the hydroformylation of the corresponding olefins can be carried out in a 1-stage process.

SUMMARY OF THE INVENTION

Thus, one object of the present invention is to combine the first three steps in the conventional processes, namely the precarbonylation, the catalyst extraction, and the hydroformylation, into a single process, and preferably into one reactor.

Another object of the present invention is to eliminate the expensive separation and reduceancy of equipment for the process stages.

Another object of the present invention is to reduce the number of process stages and thereby considerably lower the investment costs.

Another object of the present invention is to provide a process in which the precarbonylation, extraction, and hydroformylation proceed side by side and partially in situ.

Another object of the present invention is to provide a continuous process in which the cobalt salt solution is recirculated after decobalting.

The first embodiment of the present invention relates to a single-stage process that includes:
 simultaneously, in a mixture including:
  an olefin;
  synthesis gas;
  a cobalt catalyst in an organic phase; and
  an aqueous cobalt salt solution;
 hydroformylating the olefin, and forming and extracting into the organic phase the cobalt catalyst from the aqueous cobalt salt solution.

The second embodiment of the present invention relates to an apparatus that includes:
 a means for carrying out the process as described above.

The third embodiment of the present invention relates to an aldehyde, produced by the process described above.

The fourth embodiment of the present invention relates to an alcohol, produced by the process described above.

DESCRIPTION OF THE PREFERRED EMBODIMENTS

Other features of the present invention will become apparent in the course of the following descriptions of exemplary embodiments, which are given for illustration of the invention and are not intended to be limiting thereof.

Preferably, the process according to the invention produces alcohols having 7 to 18 C atoms by hydroformylation of the corresponding olefins with synthesis gas in the presence of an organic phase containing a cobalt catalyst at temperatures from 50 to 220° C. and pressures from 100 to 400 bar and subsequent hydrogenation of the aldehydes thus obtained. The cobalt catalyst is formed by reacting an aqueous cobalt salt solution in the presence of an organic solvent, which is only slightly miscible with water or not at all, with synthesis gas. The organic phase containing the cobalt catalyst being is obtained by extraction of the cobalt catalyst formed from the aqueous phase by means of an organic extractant which is only slightly miscible with water or not at all, which includes carrying out the formation of the cobalt catalyst, the extraction of the cobalt catalyst formed into the organic phase and the hydroformylation of the corresponding olefins in a 1-stage process.

Preferably, the formation of the cobalt catalyst, the extraction of the cobalt catalyst into the organic phase and the hydroformylation of the corresponding olefins are carried out in one single reactor.

In addition, the present invention relates to the use of the alcohols produced according to the invention for the production of carboxylic acid esters as plasticizers for plastics.

The process according to the invention is preferably carried out continuously.

The preferred cobalt salts used are water-soluble cobalt salts such as, for example, formates and acetates. Cobalt acetate, which is preferably employed as an aqueous solution with a cobalt content of from 0.2 to 2% by weight, particularly preferably from 0.5 to 1.5% by weight, calculated as metal, has proved particularly suitable.

The organic solvent can be the olefin to be hydroformylated and/or an aldehyde and/or an alcohol, the aldehyde and the alcohol preferably being the reaction products formed during the hydroformylation.

Thus, the organic solvent which is only slightly miscible with water or not at all is preferably an olefin and/or an aldehyde and/or an alcohol, particularly preferably the reaction product from the 1-stage process.

The organic extractant required for the extraction of the cobalt catalyst from the aqueous phase can be any organic solvent which is only slightly miscible with water or not at all, provided that it has sufficient solubility for the cobalt catalyst. However, a mixture of the olefin to be hydroformylated and the aldehydes and/or alcohols formed during the hydroformylation is preferably employed.

Thus, an olefin and/or an aldehyde and/or an alcohol, particularly preferably the reaction product from the 1-stage process, is preferably employed as the organic extractant which is only slightly miscible with water or not at all.

Suitably, the organic solvent which is only slightly miscible with water or not at all and the organic extractant which is only slightly miscible with water or not at all are identical.

Preferably, not at all miscible is taken to mean immiscible.

Particular importance is attached in the process according to the invention to the metering of the starting materials into the reactor of the 1-stage process. The metering device should ensure good phase-mixing and the generation of the largest possible phase exchange area. For the metering of the starting materials, the metering devices known in industry, such as, for example, turbulence pipes filled with packing or mixing nozzles for multi-phase systems, can be employed. The metering is preferably carried out with a mixing nozzle while maintaining turbulent flow.

The aqueous cobalt salt solution, olefin, synthesis gas, an organic solvent, which is only slightly miscible with water or not at all, and an organic extractant, which is only slightly miscible with water or not at all, can be introduced into the reactor of the 1-stage process simultaneously, in particular by means of a mixing nozzle.

In another variant of the process according to the invention, an organic solvent, which is only slightly miscible with water or not at all, and an organic extractant, which is only slightly miscible with water or not at all, can be initially introduced into the reactor of the 1-stage process, and the aqueous cobalt salt solution, olefin and synthesis gas can be fed to the reactor of the 1-stage process simultaneously, in particular by means of a mixing nozzle.

In a further embodiment of the present invention, an organic extract, which is only slightly miscible with water or not at all, can be initially introduced into the reactor of the 1-stage process, and the aqueous cobalt salt solution, olefin, synthesis gas and an organic solvent, which is only slightly miscible with water or not at all, can be fed to the reactor of the 1-stage process simultaneously, in particular by means of mixing nozzle.

Preferably, the aqueous cobalt salt solution, olefin and synthesis gas are fed simultaneously to the reactor of the 1-stage process, particularly preferably by means of a mixing nozzle.

The 1-stage process, which includes the precarbonylation, the catalyst extraction and the hydroformylation, can be carried out in a reactor at temperatures from 100 to 250° C. and under pressures from 100 to 400 bar. Temperatures from 160 to 220° C. and synthesis gas pressures from 200 to 300 bar have proved particularly suitable.

Preferably, the carbon monoxide/hydrogen volume ratio in the synthesis gas is in general between 2:1 and 1:2, more preferably 1:1. The synthesis gas is advantageously used in a slight excess over the amount stoichiometrically required for the hydroformylation.

The 1-stage process can, for example, be carried out in the generally known cylindrical upright high-pressure bubble column reactors, with or without an internally fitted coaxial insertion pipe.

In a preferred embodiment of the process according to the invention, the reactor space of the 1-stage process is subdivided by at least one partition device. This partition device can. for example, be a perforated plate or a sieve tray and is suitably arranged perpendicular to the direction of flow of the stream of reactants and products.

As a result of the cascading of the reactor, the back-mixing is greatly reduced as compared with the simple bubble column, and the flow behavior approaches that of a tubular reactor. This process engineering measure has the consequence that both the space-time yield and the selectivity of the hydroformylation are improved.

In a preferred embodiment of the process according to the invention, the reactor product (organic and aqueous phases), it being possible to take the aqueous phase off wholly or partially at the bottom of the reactor, can be let down, after leaving the reactor, to 10 to 15 bar and then passed as discharge product into the decobalting necessary for removing the cobalt catalyst. In the decobalting stage, the discharge product can be freed of cobalt carbonyl complexes in the presence of an aqueous acidic cobalt salt solution (process water) by means of air or oxygen at temperatures from 50 to 180° C. The aqueous acidic cobalt salt solution (process water) has a cobalt content from 0.2 to 2.0% by weight, calculated as metal, and a pH from 3 to 4. The pH can, for example, be adjusted with acetic acid. The decobalting can expediently be carried out at temperatures from 120 to 150° C., in order to ensure that the acetals formed by secondary reactions in the 1-stage process are broken down again as completely as possible to the desired valuable products, namely aldehyde and alcohol The decobalting is preferably carried out in a pressure vessel which is filled with packing such as, for example, raschig rings and in which the greatest possible phase exchange area is generated. The organic product phase, now freed of cobalt compounds, can be separated from the aqueous phase in a downstream separation vessel. The aqueous phase, which contains the cobalt compounds extracted from the organic phase, for example in the form of cobalt acetate or cobalt formate, is preferably recycled to the 1-stage process and again used as starting material for the preparation of the cobalt catalyst.

Preferably, the process according to the invention is thus carried out in such a way that the reactor product of the 1-stage process is treated, for the oxidation of the cobalt catalyst, with air with addition of aqueous acidic cobalt salt solution and, after separation into an organic phase containing the reactor products and an aqueous phase containing the cobalt salt, the aqueous phase is recycled to the 1-stage process.

Subsequently, the organic phase that remains after the removal of the cobalt catalyst can be hydrogenated and the alcohols thus obtained can be recovered from the hydrogenation product, for example by distillation.

Under the reaction conditions of the process according to the invention, the corresponding alcohols are also partially formed by hydrogenation in addition to the aldehydes. After the decobalting, the aldehydes and alcohols can be separated from the organic reactor product and be further processed individually. Preferably, however, the complete organic reactor product is processed to give the corresponding alcohol by known processes, for example by hydrogenation and subsequent distillation.

The alcohols produced by the process according to the invention are particularly suitable as plasticizer alcohols and detergent alcohols. The aldehydes can also be used for the production of carboxylic acids. Plasticizer alcohols are converted by esterification, for example with phthalic anhydride (PA), to the usual plasticizers for polyvinyl chloride (PVC).

By means of the process according to the invention, olefins having 6 to 17 carbon atoms, more preferably 8 to 12 carbon atoms can be hydroformylated and the aldehydes thus obtained can be hydrogenated. These olefins may be branched or unbranched and/or internal olefins.

The process according to the invention is particularly suitable for the hydroformylation of isomeric olefin mixtures which are produced by oligomerization of propene and butenes. Typical oligomerization products, which can be employed as raw material base for the hydroformylation, include for example dipropene, tripropene and tetrapropene as well as dibutene, tributene and tetrabutene.

Preferably, branched or unbranched alcohols having 7 to 18 carbon atoms, more preferably 9 to 13 carbon atoms are produced from the corresponding olefins by means of the process according to the invention, in particular isononanols from dibutenes.

The oligomerization products of n-butenes are available on a large industrial scale via the known oligomerization processes, for example the Octol® process of Huls and the Dimersol® process of IFP (J. Schulze, M. Homann: "$C_4$-Hydrocarbons and Derivates", pages 69 et seq., Springer Verlag, Berlin/Heidelberg, 1989) the entire contents of which are hereby incorporated by reference.

The aldehydes obtained in the process according to the invention can be hydrogenated to the desired alcohols by the known hydrogenation processes in the gas phase or liquid phase (SRI International, Report No. 21 C, April 1986, pages 53 et seq.) the entire contents of which are hereby incorporated by reference. Suitable catalysts for the hydrogenation of aldehydes are in particular, copper chromite catalysts, nickel catalysts and copper-zinc catalysts. In part, the hydrogenation of the aldehydes to the alcohols already takes place in the 1-stage process.

EXAMPLES

Having generally described this invention, a further understanding can be obtained by reference to certain specific examples which are provided herein for purposes of illustration only and are not intended to be limiting unless otherwise specified.

Comparison example: Conventional process for the production of isononanol from dibutene.
Precarbonylation:

1000 ml of water containing cobalt acetate (about 1.0% by weight of cobalt, calculated as metal) are initially introduced into a 2 l stirred stainless steel autoclave. Synthesis gas at a $CO/H_2$ volume ratio of 1:1 is introduced at 170° C. and 280 bar into the autoclave with stirring (1000 rpm). The formation of the cobalt carbonyl complexes during the precarbonylation can be monitored analytically by sampling offset in time. After a precarbonylation time of 6 hours, about 65% of the cobalt salt employed is converted to the active cobalt catalyst, namely the cobalt hydrocarbonyl complexes.

A marked shortening of the precarbonylation time can be obtained by addition of alcohols which are slightly miscible with water or not all, such as, for example, 2-ethylhexanol or isononanol. If the precarbonylation is carried out with a cobalt salt/water/isononanol mixture (250 ml isononanol and 750 ml of aqueous cobalt acetate solution with 1% by weight of cobalt, calculated as metal) under the abovementioned conditions, 65% conversion of the cobalt salt employed to cobalt carbonyl complexes is reached after 5 minutes.
Catalyst extraction:

After completion of the precarbonylation, the autoclave is, for carrying out the catalyst extraction, let down to a synthesis gas pressure of 100 bar and cooled to a temperature of about 60° C. Under these conditions, the cobalt carbonyl complex is extracted, after addition of 500 ml of di-n-butene, into the di-n-butene functioning as an organic phase with intensive stirring (1000 rpm). After an extraction time of about 10 minutes, the extraction mixture is left to stand for a further 10 minutes for the purpose of phase separation, with the stirrer switched off. The olefinic phase contains 0.22% by weight of cobalt as cobalt carbonyl complex ($HCo(CO)_4$). The aqueous phase contains, in addition to 0.35% by weight of cobalt as cobalt(II) salt, also about 0.57% by weight of cobalt as non-extracted cobalt carbonyl complex. This means that only about 12% of the extractable cobalt carbonyl complex was extracted into the olefinic phase.
Hydroformylation:

After the catalyst extraction, the aqueous phase is let out of the autoclave, and a further 500 ml of di-n-butene are fed in. Subsequently, the olefinic phase loaded with cobalt hydrocarbonyl complex is hydroformylated with synthesis gas at a $CO/H_2$ volume ratio of 1:1 at a temperature of 175° C. and a pressure of 260 bar. After a reaction time of 4 hours, virtually no further synthesis gas is absorbed and the hydroformylation is complete.
Decobalting:

For the decobalting, the autoclave is let down and the product mixture is cooled to about 100° C. By treating the reaction mixture with air below 100° C. in the presence of dilute acetic acid, the cobalt carbonyl complexes are oxidized and the resulting cobalt salts are extracted back into the aqueous phase.

According to an analysis by gas chromatography, the organic phase has the following composition in % by weight:

12.5% of $C_8$-hydrocarbons, 44.5% of isononanals, 29.5% of isononanols, 3.5% of esters (isononyl formates), 5% of acetals and 5% of higher boiling residue.
Hydrogenation:

The isononanals and isononyl formates are hydrogenated to the isononanols in the presence of a copper chromite catalyst at 20 to 30 bar and 150 to 250° C. in the gas phase.

Example 1
Production of Isononanols from Dibutene

The process according to the invention is carried out in a continuous pilot plant which includes a high-pressure tubular reactor (90 mm diameter, 3600 mm length) and a downstream decobalting vessel (20 L capacity) packed with raschig rings, and a phase separation vessel. The reactor space of the high-pressure reactor is cascaded by means of 5 perforated plates built in perpendicular to the direction of flow. A 3-component mixing nozzle is used for the metering of the starting materials. The reactor contents can be heated or cooled by the installed heating and cooling devices as required.

Since the precarbonylation is accelerated in the presence of an alcohol and/or aldehyde, isononanol or an isononanal/isononanol mixture can be initially introduced as a starting aid into the reactor at the beginning of the 1-stage process according to the invention. After the reactor has been brought to the operating temperature of 160 to 180° C., a di-n-butene from the Huls Octol process, aqueous cobalt acetate solution with 1% by weight of cobalt, calculated as metal, and synthesis gas at a $CO/H_2$ volume ratio of 1:1 are continuously fed to the reactor via the mixing nozzle.

The throughputs are set as follows: 5.0 kg/h of di-n-butene and 0.45 kg/h of cobalt acetate solution. The reactor is pressure-controlled with synthesis gas to a constant reaction pressure of 280 bar at a synthesis gas throughput of 2.5 to 3.5 $m^3$(s.t.p.)/h. The selected di-n-butene throughput corresponds to a space-time loading (LHSV) relative to the reactor volume of about 0.3 $h^{-1}$ (0.3 $m^3$ of di-n-butene per $m^3$ of reactor volume and per hour).

The organic phase is continuously taken off at the top of the reactor and let down to 10 to 15 bar into the decobalting stage. The aqueous phase fed as cobalt acetate solution to the reactor is taken off as process water containing cobalt complex at the bottom of the reactor under level control and likewise let down into the decobalting stage.

In the decobalting stage, the two liquid phases, together with the gas arising on the let-down (unconverted synthesis gas), are freed of cobalt catalyst by oxidation of the cobalt carbonyl complexes at 140° C. by means of air or oxygen in the presence of aqueous acidic cobalt salt solution (process water) and then separated in a downstream separation vessel. The organic cobalt-free phase is further processed, but the aqueous cobalt salt solution is recycled via the mixing nozzle to the 1-stage process. The unconverted synthesis gas is used again or discarded.

Under the selected reaction conditions, di-n-butene conversions of more than 90% are achieved.

The discharged crude product after the decobalting has, according to an analysis by gas chromatography, the following composition in % by weight: 7.0% of $C_8$-hydrocarbons, 29.7% of isononanals, 53.1% of isononanols, 4.2% of esters (isononyl formates) and 6.0% of high-boiling residue.

The high-boiling residue can very simply be separated from the valuable products by distillation.

After the decobalting, the crude product is converted to isononanol (mixture of isomers) by hydrogenation and subsequent distillation in known downstream processing steps. The hydrogenation of the crude product is carried out in the gas phase at 20 to 25 bar and 170 to 250° C. in the presence of a copper chromite catalyst.

Example 2

Production of Isotridecanol from tri-n-butene

The process according to the invention is carried out in the same way in the pilot plant described in Example 1.

Since the precarbonylation is accelerated in the presence of an alcohol and/or aldehyde, iso-tridecanol and/or an iso-tridecanol/iso-tridecanal mixture can be initially introduced as a starting aid at the beginning of the 1-stage process according to the invention.

After the reactor has been brought to the operating temperature of 160–180° C., the starting materials tri-n-butene from the Hüls Octol process, aqueous cobalt acetate solution with 1% by weight of cobalt, calculated as metal, and synthesis gas at a $CO/H_2$ volume ratio of 1:1 are continuously fed to the reactor.

The throughputs are set as follows: 1.65 kg/h of tri-n-butene and 0.15 kg/h of cobalt acetate solution. The reactor is pressure-controlled with synthesis gas to a constant reaction pressure of 280 bar and a synthesis gas throughput of 0.8 to 1.2 $m^3$(s.t.p)/h. The selected tri-n-butene throughput corresponds to a space-time load relative to the reactor volume (LHSV) of about 0.1 $h^{-1}$ (0.1 $m^3$ of tri-n-butene per $m^3$ of reactor volume and per hour).

The reactor product is further processed as described in Example 1.

Under the selected reaction conditions, tri-n-butene conversions of at least 80% are achieved.

The discharged crude product after the decobalting has, according to an analysis by gas chromatography, the following composition in % by weight 16.5% of $C_{12}$ hydrocarbons, 73.5% of iso-tridecanals and isotridecanols and 10.0% of high-boiling residue.

After the decobalting, the crude product is converted to iso-tridecanols (mixture of isomers) in downstream known processing steps by hydrogenation in the presence of a copper chromite catalyst at 20 to 30 bar and 150 to 250° C. in the liquid phase and subsequent distillation.

Obviously, numerous modifications and variations of the present invention are possible in light of the above teachings. It is therefore to be understood that within the scope of the appended claims, the invention may be practiced otherwise than as specifically described herein.

This application is based on German Patent Application 196 54 340. 1, filed Dec. 24, 1996, the entire contents of which are hereby incorporated by reference.

What is claimed as new and desired to be secured by Letters Patent of the united states is:

1. A single-stage hydroformylation process, comprising: forming a mixture comprising:

(a) an olefin;

(b) synthesis gas; and (c) an aqueous cobalt salt solution; and in a single stage forming a cobalt catalyst; extracting into said organic phase said cobalt catalyst from said aqueous cobalt salt solution; and hydroformylating said olefin.

2. The process as claimed in claim 1, further comprising hydrogenating the hydroformylated olefin into an alcohol.

3. The process as claimed in claim 2, wherein said alcohol is a $C_{7-18}$ alcohol.

4. The process as claimed in claim 3, wherein said alcohol is isononanol.

5. The process as claimed in claim 1, further comprising simultaneously feeding said aqueous cobalt salt solution, said olefin, said synthesis gas, and said organic phase into said mixture.

6. The process as claimed in claim 1, further comprising initially feeding said organic phase into said mixture, then simultaneously feeding into said mixture said aqueous cobalt salt solution, said olefin and said synthesis gas.

7. The process as claimed in claim 1, wherein said organic phase comprises an organic solvent and an organic extractant.

8. The process as claimed in claim 7, wherein said organic extractant is only slightly miscible with water or not at all, and said organic solvent is only slightly miscible with water or not at all.

9. The process as claimed in claim 8, wherein said organic extractant is selected from the group, consisting of olefins, aldehydes, alcohols, and a mixture thereof; and said organic solvent is selected from the group consisting of olefins, aldehydes, alcohols, and a mixture thereof.

10. The process as claimed in claim 1, wherein said organic phase comprises said olefin and an aldehyde formed from said hydroformylating.

11. The process as claimed in claim 10, wherein said organic phase further comprises an alcohol formed during said hydroformylating.

12. The process as claimed in claim 1, wherein said aqueous cobalt salt solution comprises a solution selected from the group consisting of cobalt acetate, cobalt formate, and a mixture thereof.

13. The process as claimed in claim 1, wherein said cobalt catalyst comprises $HCo(CO)_4$.

14. The process as claimed in claim 1, further comprising oxidizing said cobalt catalyst.

15. The process as claimed in claim 14, wherein said oxidizing comprises treating the cobalt catalyst with air and an aqueous acidic cobalt salt solution.

16. The process as claimed in claim 15, further comprising recycling the aqueous cobalt salt solution to said single-stage process.

17. The process as claimed in claim 1, carried out at a temperature of 50–250° C. and a pressure of 100–400 bar.

18. The process as claimed in claim 1, further comprising separating the hydroformylated olefin.

* * * * *